United States Patent
Streukens et al.

(10) Patent No.: US 9,029,412 B2
(45) Date of Patent: May 12, 2015

(54) METHOD FOR PREPARING DIAMINO-DIANHYDRO-DIDEOXYHEXITOLS, PARTICULARLY PREFERABLY 2,5-DIAMINO-1,4:3,6-DIANHYDRO-2,5-DIDEOXY-D-HEXITOL

(75) Inventors: Guido Streukens, Wuppertal (DE); Christian Lettmann, Coesfeld (DE); Sven Schneider, Datteln (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/809,435

(22) PCT Filed: Jun. 28, 2011

(86) PCT No.: PCT/EP2011/060825
§ 371 (c)(1),
(2), (4) Date: Jan. 10, 2013

(87) PCT Pub. No.: WO2012/010385
PCT Pub. Date: Jan. 26, 2012

(65) Prior Publication Data
US 2013/0116451 A1  May 9, 2013

(30) Foreign Application Priority Data
Jul. 23, 2010 (DE) .......................... 10 2010 038 310

(51) Int. Cl.
*C07D 493/00* (2006.01)
*C07D 493/04* (2006.01)

(52) U.S. Cl.
CPC .................................. *C07D 493/04* (2013.01)

(58) Field of Classification Search
CPC .................................................. C07D 493/464
USPC ................................................. 549/464, 494
See application file for complete search history.

(56) References Cited

U.S. PATENT DOCUMENTS

| | | | |
|---|---|---|---|
| 4,429,157 A * | 1/1984 | Disteldorf et al. | 564/446 |
| 2001/0003136 A1 * | 6/2001 | Nouwen et al. | 564/396 |
| 2004/0225156 A1 * | 11/2004 | Funke et al. | 564/448 |
| 2009/0048466 A1 | 2/2009 | Lettmann et al. | |
| 2010/0041921 A1 | 2/2010 | Lettmann et al. | |
| 2011/0269977 A1 | 11/2011 | Dingerdissen et al. | |

FOREIGN PATENT DOCUMENTS

| | | |
|---|---|---|
| WO | 2010 089171 | 8/2010 |
| WO | 2010 089223 | 8/2010 |

OTHER PUBLICATIONS

Eigenberger, G., Ullmann's Encyclopedia of Industrial Chemistry, 1992, vol. B4, VCH Publishers.*
Al-Dahhan, M.H., High Pressure Trickle-Bed Reactors: A Review, 1997, Ind. Eng. Chem. Res. 36, 3292-3314.*
WO 2010/089171 Figure 19 English Translation.*
March, J., Advanced organic chemistry: reactions, mechanisms, and structure. vol. 4. New York: John Wiley & Sons, 1992.*
Haskelberg, L. "Aminative reduction of ketones." Journal of the American Chemical Society 70.8 (1948): 2811-2812.*
Bartal, N., Modeling of a Catalytic Packed Bed Reactor and Gas Chromatograph Using COMSOL Multiphysics. Diss. Worcester Polytechnic Institute, 2009.*
Bachmann, F.,"Synthesis of hydrophilic carbohydrate-derived polyamides." Journal of Polymer Science Part A: Polymer Chemistry 30.9 (1992): 2059-2062.*
Limberg, G., et al., "Synthetic Approach to N-Alkylated 2,5-Diamino-2,5-dideoxy-1,4;3,6-dianhydroalditols by Reductive Alkylation," Synthesis, vol. 1994, No. 3, pp. 317-321, (Jan. 1, 1994) XP55006214.
Thiem, J., et al., "Synthesis and properties of polyamides derived from anhydro- and dianhydroalditols," Makromol. Chem., vol. 192, No. 9, pp. 2163-2182, (Jan. 1, 1991) XP 009076069.
Bashford, V., et al., "Anhydrides of Polyhydric Alcohols. Part XIII. The Aminoderivatives of 1:4-3:6-Dianhydro-mannitol, -sorbitol, and -L-iditol, and their Behaviour towards Nitrous Acid," Journal of the Chemical Society, Chemical Society, Letchworth, pp. 371-374, (Jan. 1, 1950) XP 009093299.
International Search Report Issued Sep. 13, 2011 in PCT/EP11/60825 Filed Jun. 28, 2011.

* cited by examiner

*Primary Examiner* — Noble Jarrell
*Assistant Examiner* — John Mauro
(74) *Attorney, Agent, or Firm* — Oblon, McClelland, Maier & Neustadt, L.L.P.

(57) ABSTRACT

Method for preparing diamino-dianhydro-dideoxyhexitols, particularly 2,5-diamino-1,4:3,6-dianhydro-2,5-dideoxy-D-hexitol.

The invention related to a method for preparing diamino-dianhydro-dideoxyhexitols, particularly preferably 2,5-diamino-1,4:3,6-dianhydro-2,5-dideoxy-D-hexitol.

1 Claim, No Drawings

METHOD FOR PREPARING DIAMINO-DIANHYDRO-DIDEOXYHEXITOLS, PARTICULARLY PREFERABLY 2,5-DIAMINO-1,4:3,6-DIANHYDRO-2,5-DIDEOXY-D-HEXITOL

The invention relates to a method for preparing diamino-dianhydro-dideoxyhexitols, particularly preferably 2,5-diamino-1,4:3,6-dianhydro-2,5-dideoxy-D-hexitol.

The preparation of diamino-dianhydro-dideoxyhexitols from the corresponding diketone (2,6-dioxabicyclo[3.3.0]octane-4,8-dione, (IV) is known e.g. from Anhydrides of polyhydric alcohols. XIII. The amino derivatives of 1,4:3,6-dianhydro-mannitol, -sorbitol, and -L-iditol and their behaviour towards nitrous acid. Journal of the Chemical Society 1950; 371-374).

DE 102009000661.3 describes a method for preparing diamino-dianhydro-dideoxyhexitols in one step and preferably in two steps by imination (a) and subsequent hydrogenation (b).

It was an object of the invention to find a method which affords high yields and simultaneously a simplified workup and removal of the catalyst.

The object is achieved by the method according to the invention.

The invention relates to a two-step method for preparing diamino-dianhydro-dideoxyhexitols from the corresponding diketone by reductive amination, by means of
(a) imination in the presence of ammonia and
(b) catalytic hydrogenation in the presence of hydrogen, characterised in that at least one fixed-bed catalyst is used in step b).

Preferred subject matter of the method according to the invention is the preparation of 2,5-diamino-1,4:3,6-dianhydro-2,5-dideoxy-D-hexitol. Of the latter, three stereoismers are known of formulae (I)-(III), 2,5-diamino-1,4:3,6-dianhydro-2,5-dideoxy-D-sorbitol, DAS (I), 2,5-diamino-1,4:3,6-dianhydro-2,5-dideoxy-D-mannitol, DAM (II) and 2,5-diamino-1,4:3,6-dianhydro-2,5-dideoxy-L-iditol, DAI (III), which are prepared from the corresponding diketone (2,6-dioxabicyclo[3.3.0]octane-4,8-dione, (IV)):

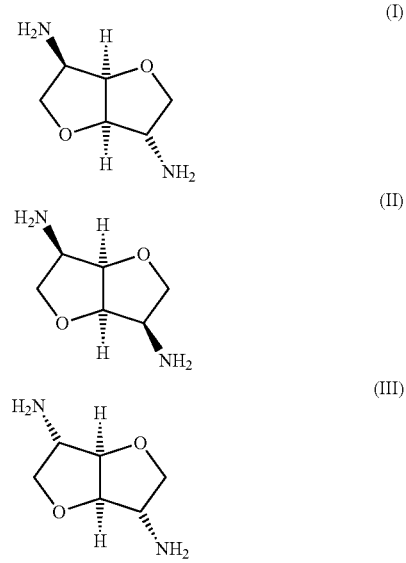

The three stereoisomers differ in regard to the chirality at positions 2 and 5. The amino groups here may be in the endo, endo (I), in the endo, exo (II) or in the exo, exo (III) position, relative to the chair form of the fused five-membered rings.

The method according to the invention takes place by the two-step reaction of the diketone (IV) to the corresponding diamines (I) to (III) by a reductive amination in the presence of ammonia and hydrogen plus a fixed-bed hydrogenation catalyst. Firstly, the diketone (IV) is converted using ammonia to the corresponding diimine (V), the subsequent hydrogenation yielding the corresponding diamine isomers (I) to (III).

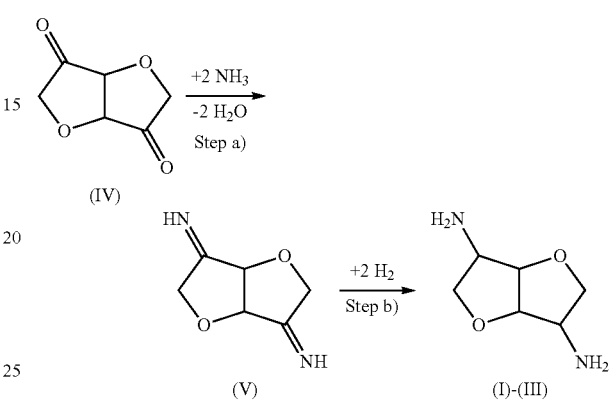

In the first step a), at least some of the starting diketone is converted to the diimine, with or without an imination catalyst and/or solvent, by reaction with ammonia.

The ammonia may be added in equimolar amounts or in excess. Ammonia is preferably added in excess with particular preference given to using a more than 10-fold excess of ammonia. The ratio of diimine to diketone after the imination should be greater than 1, preferably greater than 4 and very particularly preferably greater than 9.

In order to expedite reaching equilibrium in the imination reaction, it is preferable to use an imination catalyst. For this purpose, the imination catalysts known from the prior art may be used. Suitable catalysts are for example inorganic or organic ion exchangers (see EP 042 119), supported heteropoly acids (see DE 44 26 472), acidic metal oxides, particularly aluminium oxide and titanium dioxide (see EP 449 089), organopolysiloxanes comprising sulphonic acid groups (DE 196 27 265) and acidic zeolites. Particular preference is given to acidic ion exchangers. When using an imination catalyst the reaction temperature can be between 10 and 150° C., preferably between 15 and 120° C. and very particularly preferably between 20 and 80° C. The pressure lies between the autogenous pressure of the mixture and 500 bar. The imination reaction is preferably carried out at the pressure at which the subsequent hydrogenation is also carried out.

For the imination in the presence of an imination catalyst, the catalyst may be present in the form of a suspension catalyst or a fixed-bed catalyst. The use of fixed-bed catalysts is preferred. In a particularly preferred embodiment, diketone and ammonia are fed continuously from the bottom up through an imination catalyst-filled reaction tube. Although the imination can take place in liquid ammonia, it is preferably carried out with addition of further solvents. Suitable solvents are monohydric alcohols having 1 to 4 carbon atoms, particularly methanol, and ethers, particularly preferably tetrahydrofuran (THF), methyl tert-butyl ether (MTBE) and dioxane. Methanol is preferred.

In the second step b), the reaction product from the first step a), in the form in which it is produced after further treatment and/or addition of further ammonia, is hydrogenated in the presence of at least ammonia and hydrogen and with or without an organic solvent over the fixed-bed catalysts to be used according to the invention at a temperature of 20 to 150° C., preferably 40 to 90° C., and a pressure of 3 to 500 bar, preferably 10 to 200 bar.

The hydrogenation catalysts employed may in principle be all catalysts which catalyse the hydrogenation of imine groups with hydrogen. Particularly suitable are nickel, copper, iron, palladium, rhodium, ruthenium and cobalt fixed-bed catalysts, very particularly nickel and cobalt fixed-bed catalysts. To increase the activity, selectivity and/or service life, the catalysts additionally comprise doping metals or other modifying agents. Typical doping metals are e.g. Ti, V, Cr, Mn, Fe, Co, Ni, Mo, Ag, Ga, In, Bi and/or Zr as well as the rare earth metals. Typical modifying agents are e.g. those with which the acid-base properties of the catalysts can be influenced, such as e.g. alkali metals and alkaline earth metals or their compounds, preferably Mg and Ca compounds. Particular preference is given to moulded nickel-based and cobalt-based hydrogenation catalysts.

The catalysts are used according to the invention as random packings, such as e.g. extrudates or compressed powders. Uniform-composition catalysts, Raney-type catalysts or supported catalysts can be used. Raney-type catalysts and supported catalysts are preferred. Suitable support materials are e.g. kieselguhr, silicon dioxide, aluminium oxide, aluminosilicates, titanium dioxide, zirconium dioxide, aluminium-silicon mixed oxides, magnesium oxide and activated carbon. Aluminium oxide and silicon dioxide are preferred. The active metal can be applied to the support material in a manner known to those skilled in the art, such as e.g. by impregnation, spraying or precipitation. Depending on the type of catalyst preparation, further preparation steps known to those skilled in the art are necessary, such as e.g. drying, calcination, shaping and activation. For the shaping, further additives may optionally be added, such as e.g. graphite or magnesium stearate.

In the method according to the invention the catalysts described are used for the step b) hydrogenation of the diimine (V) and diketone (IV). This process can be conducted in a batchwise or continuous mode. The mixture added to the hydrogenation step can be directly that which arises from the imination of the diketone with ammonia in the first step a), or which is obtained after addition or removal of components, such as e.g. ammonia, organic solvents, bases, co-catalysts and/or water. The hydrogenation is preferably conducted in continuous mode in fixed-bed reactors, which may be operated in trickle mode or liquid phase mode. Suitable reactor types are e.g. shaft furnaces, tray reactors or tube bundle reactors. For the hydrogenation, it is also possible to connect a plurality of fixed-bed reactors in series, in which case each of the reactors is operated in trickle mode and liquid phase mode as required.

The hydrogen required for the hydrogenation can be added to the reactor either in excess, for example with up to 10 000 molar equivalents, or only in such an amount that the hydrogen consumed by the reaction, and also the portion of the hydrogen which leaves the reactor dissolved in the product stream, is tracked. In continuous operation mode, the hydrogen can be supplied in a co-current or counter-current manner. It is also possible to carry out the hydrogenation in the presence of the solvents already stated for the imination step.

In the method according to the invention, particular preference is given to using catalysts with the use of which an isomer distribution is attained which corresponds to a liquid end product, i.e. with a proportion of DAS of at least 40% by weight (examples 3-5).

The invention provides a liquid composition comprising 2,5-diamino-1,4:3,6-dianhydro-2,5-dideoxy-D-sorbitol, DAS (I), 2,5-diamino-1,4:3,6-dianhydro-2,5-dideoxy-D-mannitol, DAM (II) and 2,5-diamino-1,4:3,6-dianhydro-2,5-dideoxy-L-iditol, DAI (III), with a proportion of DAS (I) of at least 40% by weight.

The examples below aim to explain the invention in more detail.

EXAMPLES

Example 1

A 1 L stirred tank is charged with a solution of 75 g of the diketone in 325 g of methanol. The reactor is equipped with 146 g of Lewatit K2621 as fixed-bed catalyst. 89 g of $NH_3$ are injected and the reaction mixture is stirred for 18 h at 40° C. Subsequently the reaction mixture is transferred by means of $N_2$ positive pressure to a further 1 L stirred tank, equipped with 94 g (water-moist) of a fixed-bed nickel supported catalyst (10.3% by weight of $Ni/Al_2O_3$). The mixture is heated to 70° C. and the reaction is initiated by addition of hydrogen up to a total pressure of 50 bar. The pressure is held constant for 6 h at 50 bar. After cooling and decompressing the reactor, a mixture comprising 52% by weight of diaminomannitol, 33% by weight of diaminosorbitol and 5% by weight diaminoiditol was isolated. The total yield of diamine is 90% by weight.

Example 2

To a 5% by weight solution of the diketone in methanol is added an 80-fold molar excess of $NH_3$. This solution is fed continuously at 50 mL/h through an imination reactor. The imination reactor is equipped with 50 mL of Lewatit K2621 as catalyst and is operated in liquid phase mode. The imination reaction temperature is 50° C.

The reaction mixture, after leaving the imination reactor, is treated with $H_2$ (40 L/h at stp) and passed over a trickle bed reactor. The trickle bed reactor is equipped with 50 mL of a nickel supported catalyst (10.3% by weight $Ni/Al_2O_3$). The reaction temperature of the hydrogenation is 90° C. The overall pressure of the reaction in both reaction steps is 200 bar. The overall yield of diamine is 96% by weight. The isomer distribution of DAM, DAS and DAI is 60:35:5% by weight.

Example 3

As example 2, except that the trickle bed reactor is equipped with a nickel-copper-chromium supported catalyst (7.5% by weight Ni, 2.5% by weight Cu, 0.8% by weight $Cr/Al_2O_3$). The overall yield of diamine is 95% by weight. The isomer distribution of DAM, DAS and DAI is 46:44:10% by weight.

Example 4

As example 2, except that the trickle bed reactor is equipped with a nickel-copper supported catalyst (7.8% by weight Ni, 3.5% by weight $Cu/Al_2O_3$). The overall yield of diamine is 91% by weight. The isomer distribution of DAM, DAS and DAI is 45:44:11%.

The invention claimed is:
1. A composition, comprising 2,5-diamino-1,4:3,6-dianhydro-2,5-dideoxy-D-sorbitol, DAS (I), 2,5-diamino-1,4:3,6-dianhydro-2,5-dideoxy-D-mannitol, DAM (II) and 2,5-diamino-1,4:3,6-dianhydro-2,5-dideoxy-L-iditol, DAI (III), having a proportion of DAS (I) of at least 40% by weight.

* * * * *